(12) United States Patent
Zwick et al.

(10) Patent No.: US 12,110,637 B2
(45) Date of Patent: Oct. 8, 2024

(54) DISPERSIBLE TISSUE LAMINATE

(71) Applicant: Kimberly-Clark Worldwide, Inc., Neenah, WI (US)

(72) Inventors: Kenneth J. Zwick, Neenah, WI (US); Nicholas S. Wolter, Greenville, WI (US); Eric Hartl, Appleton, WI (US); Stephen J. Ratajczak, Neenah, WI (US); Daniel M. Piette, Neenah, WI (US); Robert S. Monson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/028,381

(22) PCT Filed: Sep. 25, 2020

(86) PCT No.: PCT/US2020/052669
§ 371 (c)(1),
(2) Date: Mar. 24, 2023

(87) PCT Pub. No.: WO2022/066164
PCT Pub. Date: Mar. 31, 2022

(65) Prior Publication Data
US 2023/0366155 A1    Nov. 16, 2023

(51) Int. Cl.
*D21H 27/32*    (2006.01)
*D21H 11/04*    (2006.01)
*D21H 27/00*    (2006.01)

(52) U.S. Cl.
CPC ............. *D21H 27/32* (2013.01); *D21H 11/04* (2013.01); *D21H 27/005* (2013.01)

(58) Field of Classification Search
CPC ...... D21H 27/002; D21H 27/38; D21H 27/32; D21H 27/30; D21H 27/02; D21H 27/005;
(Continued)

(56) References Cited

U.S. PATENT DOCUMENTS

| | | | |
|---|---|---|---|
| 5,607,551 A | 3/1997 | Farrington, Jr. et al. | |
| 5,906,711 A | 5/1999 | Barnholtz | |

(Continued)

FOREIGN PATENT DOCUMENTS

| | | |
|---|---|---|
| EP | 0782644 B1 | 11/2001 |
| EP | 1312466 B1 | 6/2006 |
| WO | 2021061128 A1 | 4/2021 |

OTHER PUBLICATIONS

LDDAVIS, "Glue Used for Paper Towel Manufacturing", https://blog.lddavis.com/glue-used-tissue-paper-towel-manufacturing.
(Continued)

*Primary Examiner* — Jose A Fortuna
(74) *Attorney, Agent, or Firm* — KIMBERLY-CLARK WORLDWIDE, INC.

(57) ABSTRACT

Dispersible adhesively bonded wet tissue laminates comprising two or more adhesively bonded tissue plies. The first and second tissue plies may be adhesively bonded to one another discrete bond points by adhesive, such as a triggerable adhesive binder. The first and second tissue plies may differ in respect to at least one of basis weight, sheet bulk, tensile strength or fiber composition. The adhesively bonded wet tissue laminates are generally strong enough to withstand use, such as having a geometric mean wet tensile strength (GMWT) greater than about 200 g/in, but disperse quickly in water, such as having a Slosh Time less than about 60 minutes.

27 Claims, 4 Drawing Sheets

(58) Field of Classification Search
CPC .......... D21H 27/40; D21H 11/04; B32B 5/26; B32B 7/12; B32B 2307/54; B32B 37/1207; D21F 11/00; A47K 10/16; A61K 8/0208; A61Q 19/10
See application file for complete search history.

(56) References Cited

U.S. PATENT DOCUMENTS

| | | | |
|---|---|---|---|
| 5,919,556 A | 7/1999 | Barnholtz | |
| 6,162,327 A | 12/2000 | Batra et al. | |
| 6,187,141 B1 | 2/2001 | Takeuchi et al. | |
| 6,309,731 B1 | 10/2001 | Takeuchi et al. | |
| 6,395,133 B1 | 5/2002 | McNeil | |
| 6,878,238 B2 | 4/2005 | Bakken et al. | |
| 6,924,042 B2* | 8/2005 | Von Paleske | B32B 9/02 428/511 |
| 7,211,171 B2* | 5/2007 | Reinheimer | B32B 5/30 428/156 |
| 8,455,077 B2 | 6/2013 | Vinson et al. | |
| 9,719,213 B2 | 8/2017 | Miller, IV et al. | |
| 10,351,998 B2* | 7/2019 | Baer | D21H 11/12 |
| 11,220,790 B2* | 1/2022 | Cabell | D21H 27/38 |
| 11,591,752 B2* | 2/2023 | McKee | D21H 27/002 |
| 11,642,868 B2* | 5/2023 | Monson | B32B 5/26 428/292.7 |
| 11,708,668 B2* | 7/2023 | Cabell | D21F 11/16 162/129 |
| 11,904,592 B2* | 2/2024 | Monson | A47K 10/16 |
| 2011/0008631 A1 | 1/2011 | Lindqvist | |
| 2012/0160436 A1 | 6/2012 | Zwick et al. | |
| 2012/0297560 A1 | 11/2012 | Zwick et al. | |
| 2015/0330029 A1 | 11/2015 | Ramaratnam et al. | |
| 2016/0067118 A1 | 3/2016 | Hammons et al. | |
| 2018/0140529 A1 | 5/2018 | Miller, IV et al. | |
| 2018/0209101 A1* | 7/2018 | Cabell | D21F 11/16 |
| 2019/0021553 A1 | 1/2019 | Saas et al. | |
| 2019/0226149 A1 | 7/2019 | Vogel et al. | |
| 2019/0366677 A1 | 12/2019 | Kleinwaechter et al. | |
| 2022/0332085 A1* | 10/2022 | Monson | D21H 27/002 |
| 2022/0364308 A1* | 11/2022 | Young | D21H 21/22 |
| 2023/0234330 A1* | 7/2023 | Monson | D21H 17/66 428/292.7 |
| 2023/0366155 A1* | 11/2023 | Zwick | D21H 27/005 |
| 2024/0149555 A1* | 5/2024 | Monson | D21H 27/32 |

OTHER PUBLICATIONS

KAPPASIL, "KAPPASIL glues for high-standard lamination", Stockmeier, https://www.stockmeier.com/en/products/tissue-textile/tissue/glues/.
Amazon, "Amazon Brand—Solimo 2 Ply Kitchen Tissue Paper Roll—4 Rolls (60 Pulls Per Roll)", https://www.amazon.in/Amazon-Brand-Solimo-Kitchen-Tissue/dp/B07MJF5THB.

* cited by examiner

DISPERSIBLE TISSUE LAMINATE

BACKGROUND

Pre-moistened wipes are popular in the marketplace, including, for example, baby wipes, surface cleaning wipes, feminine wipes, and child and adult toileting wipes. Consumers flush many of these wipes down the toilet. Some of the wipes are designed to be flushed and labeled as such. It is important that wipes that are intended to be flushed are compatible with sewer and septic systems, but also important that such wipes do not fall apart when used for their intended purpose. Specifically, when a flushable wipe is flushed down a toilet, the product, or designated portions of the product, should degrade or lose strength as it moves through various steps of wastewater processing.

One common approach to making a flushable wet wipe is using "hydroentangling" technology, in which fibers, primarily or exclusively cellulosic fibers, are "entangled" together using very small high-pressure water jets. However, some wipes made with this technology require a substantial amount of agitation to break apart after flushing, and some wipes, if made to have a very high initial strength, may not lose significant strength in relatively static environments.

Another conventional approach to making a wet wipe that exhibits satisfactory in-use strength, but that adequately breaks down in sewer or septic systems, is via the use of a binder on a substrate comprising cellulose fibers. The binder attaches to cellulose fibers, and bonds those fibers together in a network to deliver in-use strength. The binder is stable and delivers this strength when soaking in a stabilizing solution but swells and weakens in the tap water of the toilet and sewer system, thus allowing the fiber network to break apart. The strength of the wet tissue laminate can be manipulated by varying the amount of binder used and the process conditions by which the binder is applied, such as how and when it is applied to the wet tissue laminate, and by varying how the binder is dried/cured.

One variant of such a binder/stabilizing solution is a salt-sensitive triggerable binder, such as that disclosed in U.S. Pat. No. 6,994,865. The binder holds the fibers of the wet wipe together when soaked in a salt solution, which stabilizes the binder, but when washed away, causes the binder to lose fail and the wipe to lose strength. However, such binders can be relatively expensive, and it can be challenging to achieve the right balance of in-use strength and post-flush degradation when using such binders. For example, the binder add-on level can be reduced to improve dispersibility and reduce cost, but in-use strength (during toileting) can suffer. Conversely, the binder add-on can be increased to improve in-use performance (during toileting), but dispersibility can suffer, and cost increases.

What is needed is a cellulose-based wipe that combines sufficient in-use strength, adequate strength loss after flushing even in relatively non-turbulent water, and that is cost-effective.

SUMMARY

The present invention provides a dispersible tissue laminate and more particularly a dispersible multi-ply wet tissue product comprising a first tissue ply and a second tissue ply adhered to one another by an adhesive such as a triggerable binder. In particularly preferred embodiments plies are joined together at discrete bond points. The bond points may be formed by a combination of adhesive, pressure and/or temperature.

In particularly preferred embodiments the tissue products of the present invention are provided in a wet format, i.e., they contain a wetting composition added to a dry tissue laminate at add-ons ranging from about 10 to about 600 percent, based upon the weight of the dry tissue laminate. Despite being wet, the products are relatively strong, such as having s a geometric mean wet tensile strength (GMWT) greater than about 200 g/in and still more preferably at least about 250 g/in, yet are readily dispersed when flushed, such as having a Slosh Time less than about 60 minutes.

In other embodiments, the present invention provides a dispersible tissue laminate comprising a first tissue ply and a second tissue ply wherein the first and second tissue plies differ in at least one respect, such as tensile strength, which may be measured as the geometric mean tensile (GMT) strength, basis weight, sheet bulk or fiber composition. For example, the present invention provides a dispersible tissue laminate comprising a first tissue ply having a first geometric mean tensile strength (GMT) and a second tissue ply having a second GMT, wherein the second GMT is greater than the first GMT, an adhesive and a wetting agent.

In another embodiment, the present invention provides a bonded wet tissue laminate comprising a first wet-laid tissue ply and a second wet-laid tissue ply arranged in facing relation to one another and a binder disposed there between wherein the binder binds the plies together at discrete locations. In particularly preferred instances the tissue plies differ in at least one regard. For example, one ply may comprise at least about 80 percent, by dry weight of the ply, Southern softwood kraft fibers and the other ply may comprise at least about 80 percent, by dry weight of the ply, Northern softwood kraft fibers. In other instances the wet-laid tissue plies may differ with regards to basis weight, sheet bulk, or geometric mean tensile strength.

In yet other embodiments, the present invention provides a dispersible tissue laminate comprising a first wet-laid tissue ply and a second wet-laid tissue ply, wherein the first and second tissue plies are arranged in facing relationship with one another and bonded together at a plurality of discrete bond points by an adhesive disposed therebetween. The discrete bond points may be formed by supporting at least one of the tissue plies on a topographical belt having a plurality of discrete protuberances disposed on its sheet contacting surface and passing the tissue ply through a nip while supported by the topographical belt. Without wishing to be bound by any particular theory by bonding the tissue plies together at discrete locations adheres the plies together to provide sufficient strength in use but facilitates break-up when the product is flushed. Further, by bonding the plies at discrete locations the handfeel of the product may be improved, particularly the bulk of the product, particularly when wetted with a wetting agent.

In another embodiment, the present invention provides a dispersible tissue laminate comprising a first wet-laid tissue ply comprising at least about 80%, by weight dry weight of the tissue ply, Southern softwood kraft pulp and having a GMT of about 900 g/3" or less and a second wet-laid tissue ply comprising at least about 80%, by weight dry weight of the tissue ply, Northern softwood kraft pulp and having a GMT of about 1,200 g/3" or greater, an adhesive and a wetting agent, wherein the first and second tissue plies are bonded together at discrete bond points by an adhesive disposed therebetween. In yet other embodiments a method of making a dispersible adhesively bonded wet tissue laminate (a) providing a first wet-laid tissue ply having a first and a second surface and a GMT of about 900 g/3" or less; (b) providing a second wet-laid tissue ply having a first and a second surface and a GMT of about 1,200 g/3" or greater; (c) applying an adhesive to the first surface of the first wet-laid tissue ply; (d) conveying the second wet-laid tissue ply on a continuous belt having a topographical upper surface comprising at least about 10 protuberances/cm$^2$; (e) bringing the first surface of the first wet-laid tissue ply into facing relation with the first surface of the second wet-laid tissue ply; (f) passing the first and second wet-laid tissue plies through a nip to form and adhesively bonded tissue laminate; and (g) applying a wetting composition wetting composition to the adhesively bonded tissue laminate.

DEFINITIONS

As used herein the term "Machine Direction" or "MD" generally refers to the direction in which a tissue ply or product is produced. The term "Cross-Machine Direction" or "CD" refers to the direction perpendicular to the machine direction.

As used herein the term "Basis Weight" generally refers to the conditioned weight per unit area of a product, web, sheet or ply, and is generally expressed as grams per square meter (gsm). Basis weight is measured as described in the Test Methods section below.

As used herein, the term "Caliper" refers to the thickness of a product, web, sheet or ply, typically having units of millimeters (mm) and may be measured in either the wet or the dry state as described in the Test Methods section below.

As used herein, the term "Sheet Bulk" refers to the quotient of the caliper divided by the basis weight and having units of cubic centimeters per gram (cc/g).

As used herein, the term "Cup Crush" refers to one measure of the softness of a product, web, sheet or ply that is determined according to the "cup crush" test as described in U.S. Pat. No. 6,946,413, the contents of which are incorporated herein in a manner consistent with the present invention. The cup crush test measures the total energy required to crush a sample over a 4.5 cm range beginning about 0.5 cm below the top of the fabric cup. Cup crush energy generally has units of gram-force (gf). A lower cup crush value indicates a softer material. Products are typically tested as-is without conditioning or cutting. Cup crush values of laminates prepared according to the present invention may vary depending on the wet tensile strength of the laminate, however, in certain instances the laminates may have a cup crush value of about 75 gf or less, such as about 70 gf or less, such as from about 50 to about 75 gf.

As used herein, the term "Geometric Mean Tensile" (GMT) refers to the square root of the product of the machine direction tensile strength and the cross-machine direction tensile strength of a ply or a product. GMT may be measured in either a dry or wet state, as described in the Test Methods section below. Generally GMT measured in the wet state will be described as Geometric Mean Wet Tensile (GMWT) and may include a description of how long the sample was soaked prior to testing. If a wet tensile value does not specify a soak time it is assumed that the product was tested as-is, without soaking.

As used herein, the term "Ply" refers to a discrete product element. Individual plies may be arranged in juxtaposition to each other. The term may refer to a plurality of web-like components such as in an adhesively bonded tissue laminate, which may comprise two, three, four or more individual plies arranged in juxtaposition to each other where one or more plies may be attached to one another such as by an adhesive.

As used herein, the term "Protuberance" refers to a three dimensional element disposed on the sheet contacting surface of a topographical belt useful in the manufacture of laminates of the present invention. Generally the upper surface plane of a protuberance forms the upper most surface plane of the sheet contacting surface of the belt. In certain instances a protuberance may be formed by one or more warp filaments overlaying a plurality of shute filaments. In other instances a protuberance may be a nonwoven material disposed on the sheet contacting surface of the belt.

As used herein, the term "Protuberance Height" generally refers to the distance from the upper most (top) plane of a topographical belt useful in the manufacture of laminates of the present invention to another specified z-direction plane in the belt, such as the predominate upper surface plane of the belt.

As used herein, the term "Discrete" when referring to a bond, such as an adhesive bond, formed between two juxtaposed tissue plies means that the bond is unconnected from other bonds and does not extend continuously in either the machine or cross-machine direction of the bonded tissue laminate.

As used herein the term "Pattern" when referring to the deposition of an adhesive on a tissue ply or the arrangement of bond points within a product generally refers a regular, non-random, arrangement that is repeated throughout at least one dimension of the ply or product.

As used herein, the term "Wet-Laid Tissue Ply" generally refers to a tissue ply that has been manufactured by forming an aqueous suspension of papermaking fibers, depositing the aqueous suspension on a travelling, water pervious, forming fabric to form a fibrous ply and draining water through the fabric to partially dewater the fibrous ply.

As used herein, the term "Triggerable Binder" generally refers a composition capable of adhering two tissue plies together to create a laminate according to the present invention that is insoluble in a wetting composition comprising an insolubilizing agent but is dispersible or soluble in disposal water such as that found in the toilet tank, toilet bowl, or waste water system. In certain instances the triggerable binder may be a "salt triggerable binder" that is insoluble in a wetting composition comprising a predetermined concentration of sodium chloride, sodium sulfate, sodium citrate, potassium, or other mono or divalent salt acting as the insolubilizing agent, but is dispersible or soluble in disposal water such as that found in the toilet tank, toilet bowl, or waste water system. In certain non-limiting embodiments, the triggerable binders may comprise the polymerization product of a vinyl-functional cationic monomer, a hydrophobic vinyl monomer with a methyl side chain, and one or more hydrophobic vinyl monomers with alkyl side chains of 1 to 4 carbon atoms, such as disclosed in U.S. Pat. No. 7,157,389, the contents of which are incorporated herein in a manner consistent with the present disclosure.

DETAILED DESCRIPTION

Figure 1:
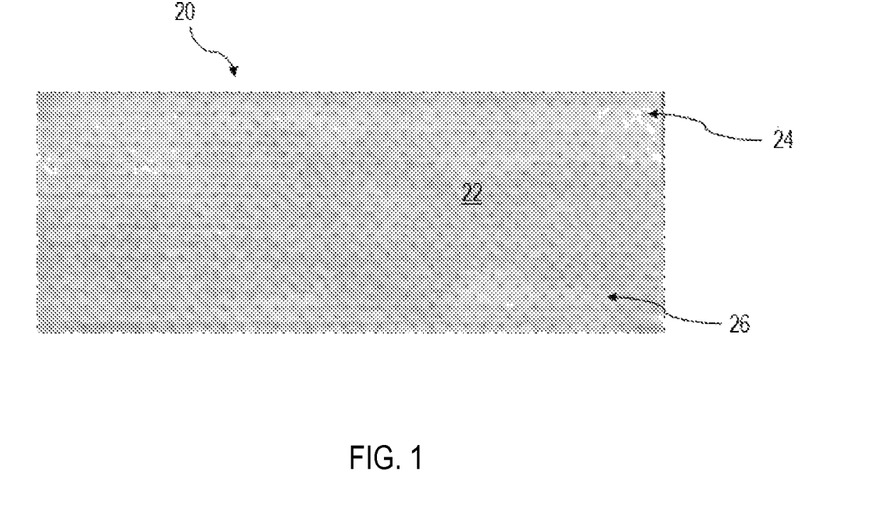
FIG. 1 is a top plane view of a dispersible wet wipe of the present invention.

The present disclosure generally relates to dispersible wet tissue laminates and more particularly dispersible wet wipes comprising two or more adhesively bonded tissue plies. For example, in certain embodiments, a wet wipe of the present invention may comprise first and second tissue plies adhesively bonded to one another by an adhesive disposed at the interface of the plies. In a particularly preferred embodiment the adhesive binds the tissue plies together at discrete bond points, the size and density of which may be controlled by varying manufacturing processes as described herein. The resulting tissue laminate 20, as illustrated in the embodiment of FIG. 1, has an upper surface 22 with visible discrete bond points 24 that are generally bounded by unbonded areas 26.

Bonding methods useful in the present invention include mechanical entanglement, hydrodynamic entanglement, needle punching, and chemical bonding and/or adhesive bonding; however, point bonding utilizing pressure and adhesive are preferred and point bonding using pressure, heat and adhesive being particularly preferred. In certain instances point bonding involves applying heat and pressure to discrete locations to form bond sites on the tissue laminate by supporting at least one ply on a topographical belt as it is conveyed through a heated and pressurized nip. In a particularly preferred embodiment the supported ply is adhesively treated prior to passing through the nip.

While it is generally preferred that the point bonds be discrete, the actual bond sites may include a variety of shapes and sizes; including but not limited to oval, round and four sided geometric shapes. The total overall bonded area may range from about 2% and about 60%, such as from about 4% to about 35%, such as from about 5% and 30%, such as from about 8% and 20%. The density of discrete point bonds may range from about 5 to about 100 bonds/$cm^2$, such as from about 10 to about 80 bonds/$cm^2$, such as from about 20 to about 60 bonds/$cm^2$.

The plies to be bonded together to form laminates of the present invention generally comprise fibrous tissue plies and more preferably wet-laid tissue comprising cellulosic fibers such as Northern or Southern softwood kraft pulp fibers. While in certain embodiments it may be preferred that the tissue plies comprise Northern or Southern softwood kraft pulp fibers, other well-known cellulosic fibers may be used. For example, the tissue plies may comprise wood or non-wood cellulosic fibers, including both bleached and unbleached fibers, virgin and recovered or recycled fibers. Particularly preferred papermaking fibers include hardwood and softwood fibers that have been mechanically pulped (e.g., groundwood), chemically pulped (including but not limited to the kraft and sulfite pulping processes), thermo-mechanically pulped, chemithermomechanically pulped, and the like. In certain instances it may be preferable to form the plies entirely from cellulosic fibers such that the plies are substantially free from synthetic fibers, such as thermoplastic fibers, particularly spunbound or meltblown thermoplastic fibers.

In certain embodiments the fiber composition of the first and the second tissue plies may differ. For example, the first tissue ply may comprise at least about 50%, by dry weight of the ply, Southern softwood kraft pulp fibers, such as at least about 60%, such as at least about 70%, such as at least about 80% by weight Southern softwood kraft pulp fibers and the second tissue ply may comprise at least about 50%, by dry weight of the ply, Northern softwood kraft pulp fibers, such as at least about 60%, such as at least about 70%, such as at least about 80% by weight Northern softwood kraft pulp fibers. In a particularly preferred embodiment the first ply consist essentially of Southern softwood kraft pulp fibers and the second ply may consist essentially of Northern softwood kraft pulp fibers.

While in certain embodiments it may be preferable to form the tissue plies entirely from a single fiber type, such as softwood kraft pulp fibers, in other instances the plies may combine two or more fiber types. For example, a headbox may be stratified to permit production of a multi-layered structure from a single headbox jet in the formation of a fibrous web. In particular embodiments, the web is produced with a stratified or layered headbox to preferentially deposit shorter fibers on one side of the web for improved softness, with relatively longer fibers on the other side of the web or in an interior layer of a web having three or more layers. The web is desirably formed on an endless loop of foraminous forming fabric which permits drainage of the liquid and partial dewatering of the web.

Generally, the laminates of the present invention do not contain nonwoven materials such as meltblown, coform, airlaid, bonded-carded web materials, hydroentangled materials, spunlace materials, and combinations thereof. Rather, the laminates are formed by adhesively bonding cellulosic tissue plies, particularly wet-laid tissue plies comprising wood pulp fibers, in facing arrangement with one another such that all of the plies forming the product consist of tissue plies and more particularly wet-laid tissue plies.

Tissue plies useful in the present invention may be manufactured using any one of a variety of well-known wet-laid papermaking processes such as, for example, creped wet pressed, modified wet pressed, creped through-air dried (CTAD) or uncreped through-air dried (UCTAD). For example, a creped tissue ply may be formed using either a wet pressed or modified wet pressed process such as those disclosed in U.S. Pat. Nos. 3,953,638, 5,324,575 and 6,080,279, the disclosures of which are incorporated herein in a manner consistent with the instant application. In these processes the embryonic tissue web is transferred to a Yankee dryer, which completes the drying process, and then creped from the Yankee surface using a doctor blade or other suitable device.

In other instances, the tissue plies are made by a through-air dried process known in the art. In such processes the embryonic web is noncompressively dried. For example, textured tissue plies may be formed by either creped or uncreped through-air dried processes. Particularly preferred are uncreped through-air dried webs, such as those described in U.S. Pat. No. 5,779,860, the contents of which are incorporated herein in a manner consistent with the present disclosure.

In still other instances the tissue plies may be manufactured by a process including the step of using pressure, vacuum, or air flow through the wet web (or a combination of these) to conform the wet web into a shaped fabric and subsequently drying the shaped sheet using a Yankee dryer, or series of steam heated dryers, or some other means, including but not limited to tissue made using the ATMOS process developed by Voith or the NTT process developed by Metso; or fabric creped tissue, made using a process including the step of transferring the wet web from a carrying surface (belt, fabric, felt, or roll) moving at one speed to a fabric moving at a slower speed (at least 5 percent slower) and subsequently drying the sheet. Those skilled in the art will recognize that these processes are not mutually exclusive, e.g., an uncreped TAD process may include a fabric crepe step.

The instant multi-ply tissue product may be constructed from two or more plies that are manufactured using the same or different tissue making techniques. In a particularly preferred embodiment, the multi-ply tissue product comprises two or more plies, such as two, three or four plies where each of the plies are through-air dried tissue plies and more preferably uncreped through-air dried plies.

Generally the basis weight of each of the dry tissue plies is greater than about 10 gsm, such as from about 15 to about 60 gsm, such as from about 25 to about 50 gsm. In certain embodiments it may be preferable that the first and second tissue plies have different basis weights, such as basis weights that differ by at least about 25%, more preferably at least about 30% and still more preferably at least about 50%, such as from about 25 to about 100%. For example, the first tissue ply may have a basis weight from about 25 to about 30 gsm and the second tissue ply may have a basis weight that is from about 45 to about 50 gsm.

In other embodiments the it may be preferable that the first and second tissue plies have different tensile strengths, such as tensile strengths that differ by at least about 30%, more preferably at least about 60% and still more preferably at least about 90%, such as from about 30 to about 150%, such as from about 50 to about 120%. For example, the first tissue ply may have a dry geometric mean tensile strength (GMT) of about 900 g/3" or less, such as from about 600 to about 900 g/3" gsm, such as from about 650 to about 800 g/3" and the second tissue ply may have a GMT of about 1,200 g/3" or greater, such as from about 1,200 to about 2,000 g/3", such as from about 1,400 to about 1,800 g/3".

Generally each of the plies have first and second surface that may be arranged to bring the plies into facing relation with another to form a product. An adhesive may be applied to at least one the ply faces such that when the plies are brought together in facing relation the adhesive binds the plies together along the interface. In particularly preferred embodiments the adhesive binds the plies together at discrete locations as a result of one of the plies being supported by a topographical belt as the plies are brought together and passed through a nip.

Prior to the plies being brought together an adhesive may be applied to one or both of the outer surfaces of the first and second tissue plies. In particular embodiments, the binder is applied as randomly distributed deposits binder on each of the outer surfaces. "Randomly distributed deposits" as used herein means that the elements of binder that form the coating are applied without any predetermined pattern, but are instead randomly applied in a continuous, uninterrupted operation, such as via a continuous mist spray, a continuous rotary print coater, a continuous brush coater, or the like. It is understood that at a microscopic level, the deposits of binder may have space between them; "randomly distributed deposits" is meant to distinguish from, for example, an application having a distinct, predetermined, repeating pattern that is visible to the naked eye.

The adhesive may be applied in a random pattern to one or both of the tissue ply outer surfaces by a continuous, uninterrupted operation, such as via a continuous mist spray, a continuous rotary print coater, a continuous brush coater, or the like.

The percentage of the outer ply surface area that is treated with binder may vary. "Binder surface area" as used herein means the area bounded by the cumulative footprint upon which the binder is applied, without regard to the microscopic space between individual deposits of binder. In particular embodiments, the binder surface area at most 75 percent, at most 50 percent, at most 25 percent.

Just as the surface area of the ply treated with binder may vary, the amount of binder applied to one or more of the tissue plies may also vary. In certain embodiments, the amount of binder applied to one or more of the tissue plies may be about 1.5 grams per square meter (gsm) or more, such as 2.0 gsm or more, such as about 4.0 gsm or more. In certain embodiments, binder is applied to an outer surface of first and second tissue plies and the total binder add-on is from about 3.0 to about 15 gsm, such as from about 4.0 to about 10 gsm.

In particularly preferred embodiments, the adhesive is a triggerable binder. A variety of triggerable binders may be used. One type of triggerable binder is a dilution triggerable binder. Examples of dilution triggerable binders include ion-sensitive polymers, which may be employed in combination with a wetting composition in which the insolubilizing agent is a salt. Other dilution triggerable binders may also be employed, wherein these dilution triggerable binders are used in combination with wetting agents using a variety of insolubilizing agents, such as organic or polymeric compounds.

Although the triggerable binder may be selected from a variety of polymers, including temperature sensitive polymers and pH-sensitive polymers, the triggerable binder may preferably be the dilution triggerable binder, comprising the ion-sensitive polymer. If the ion-sensitive polymer is derived from one or more monomers, where at least one contains an anionic functionality, the ion-sensitive polymer is referred to as an anionic ion-sensitive polymer. If the ion-sensitive polymer is derived from one or more monomers, where at least one contains a cationic functionality, the ion-sensitive polymer is referred to as a cationic ion-sensitive polymer. An exemplary anionic ion-sensitive polymer is described in U.S. Pat. No. 6,423,804, which is incorporated herein in its entirety by reference.

Examples of cationic ion-sensitive polymers are disclosed in the following U.S. Patent Application Publication Nos.: 2003/0026963, 2003/0027270, 2003/0032352, 2004/0030080, 2003/0055146, 2003/0022568, 2003/0045645, 2004/0058600, 2004/0058073, 2004/0063888, 2004/0055704, 2004/0058606, and 2004/0062791, all of which are incorporated herein by reference in their entirety, except that in the event of any inconsistent disclosure or definition from the present application, the disclosure or definition herein shall be deemed to prevail.

Desirably, the ion-sensitive polymer may be insoluble in the wetting composition, wherein the wetting composition comprises at least about 0.3 weight percent of an insolubilizing agent which may be comprised of one or more inorganic and/or organic salts containing monovalent and/or divalent ions. More desirably, the ion-sensitive polymer may be insoluble in the wetting composition, wherein the wetting composition comprises from about 0.3 to about 3.5 percent by weight of an insolubilizing agent which may be comprised of one or more inorganic and/or organic salts containing monovalent and/or divalent ions. Even more desirably, the ion-sensitive polymer may be insoluble in the wetting composition, wherein the wetting composition comprises from about 0.5 to about 3.5 percent by weight of an insolubilizing agent which comprises one or more inorganic and/or organic salts containing monovalent and/or divalent ions. Especially desirable, the ion-sensitive polymer may be insoluble in the wetting composition, wherein the wetting composition comprises from about 1 to about 3 percent by weight of an insolubilizing agent which comprises one or more inorganic and/or organic salts containing monovalent and/or divalent ions. Suitable monovalent ions include, but are not limited to, Na+ ions, K+ ions, Li+ ions, NH4+ ions, low molecular weight quaternary ammonium compounds (e.g., those having fewer than 5 carbons on any side group), and a combination thereof. Suitable divalent ions include, but are not limited to, Zn2+, Ca2+ and Mg2+. These monovalent and divalent ions may be derived from organic and inorganic salts including, but not limited to, NaCl, NaBr, KCl, N H4Cl, Na2SO4, ZnCl2, CaCl2, MgCl2, MgSO4, and combinations thereof. Typically, alkali metal halides are the most desirable monovalent or divalent ions because of cost, purity, low toxicity, and availability. A desirable salt is NaCl.

In a preferred embodiment, the ion-sensitive polymer may desirably provide the wet tissue laminate substrate with sufficient in-use strength (typically >300 grams per linear inch) in combination with the wetting composition containing sodium chloride. These wipe substrates may be dispersible in tap water, desirably losing most of their wet strength (<200 grams per linear inch) in one hour or less.

In another preferred embodiment, the ion-sensitive polymer may comprise the cationic sensitive polymer, wherein the cationic sensitive polymer is a cationic polyacrylate that is the polymerization product of 96 mol % methyl acrylate and 4 mol % [2-(acryloyloxy)ethyl]trimethyl ammonium chloride.

In certain instances, the adhesive may comprise a triggerable binder and/or the co-binder. When the binder composition comprises the triggerable binder and the co-binder, the triggerable binder and the co-binder may preferably be compatible with each other in aqueous solutions to: 1) allow for facile application of the binder composition to the fibrous substrate in a continuous process and 2) prevent interference with the dispersibility of the binder composition. Therefore, if the triggerable binder is the anionic ion-sensitive polymer, co-binders which are anionic, nonionic, or very weakly cationic may be preferred. If the triggerable binder is the cationic ion-sensitive polymer, co-binders which are cationic, nonionic, or very weakly anionic may be added. Additionally, the co-binder desirably does not provide substantial cohesion to the wet tissue laminate substrate by way of covalent bonds, such that it interferes with the dispersibility of the wet tissue laminate substrate.

The presence of the co-binder may provide a number of desirable qualities. For example, the co-binder may serve to reduce the shear viscosity of the triggerable binder, such that the binder composition may be more easily sprayed compared to the triggerable binder alone. By use of the term "sprayable" it is meant that these polymers may be applied to the fibrous material or substrate by spraying, allowing the uniform distribution of these polymers across the surface of the substrate and penetration of these polymers into the substrate. The co-binder may also reduce the stiffness of the wet tissue laminate compared to the stiffness of a wipe substrate to which only the triggerable binder has been applied. Reduced stiffness may be achieved if the co-binder has a glass transition temperature ($T_g$), which is lower than the $T_g$ of the triggerable binder. In addition, the co-binder may be less expensive than the triggerable binder and by reducing the amount of triggerable binder needed, may serve to reduce the cost of the binder composition. Thus, it may be desirable to use the highest amount of co-binder possible in the binder composition such that it does not jeopardize the dispersibility and in-use strength properties of the wet wipe. In a preferred embodiment, the co-binder replaces a portion of the triggerable binder in the binder composition and permits a given strength level to be achieved, relative to a wet wipe having approximately the same tensile strength but containing only the triggerable binder in the binder composition, to provide at least one of the following attributes: lower stiffness, better tactile properties (e.g. lubricity or smoothness), or reduced cost.

In one embodiment, the co-binder present in the binder composition, relative to the mass of the binder composition, may be about 10 percent or less, more desirably about 15 percent or less, more desirably 20 percent or less, more desirably 30 percent or less, or more desirably about 45 percent or less. Exemplary ranges of co-binder relative to the solid mass of the binder composition may include from about 1 to about 45 percent, from about 25 to about 35 percent, from about 1 to about 20 percent and from about 5 to about 25 percent.

The co-binder may be selected from a wide variety of polymers, as are known in the art. For example, the co-binder may be selected from the group consisting of poly (ethylene-vinyl acetate), poly(styrene-butadiene), poly(styrene-acrylic), a vinyl acrylic terpolymer, a polyester latex, an acrylic emulsion latex, polyvinyl chloride), ethylene-vinyl chloride copolymer, a carboxylated vinyl acetate latex, and the like. A variety of additional exemplary co-binder polymers are discussed in U.S. Pat. No. 6,653,406 and U.S. Patent Application Publication No. 2003/00326963, which are both incorporated herein by reference in their entirety. Particularly preferred co-binders include Airflex® EZ123 and Airflex® 110.

The wet tissue laminate further includes a wetting composition. The wetting composition may include a first insolubilizing agent, and optionally a second insolubilizing agent. Desirably, the adhesive is insoluble (stable) in the presence of the wetting composition containing one or more insolubilizing agents. In other words, the one or more insolubilizing agents render stable the adhesive, prior to the wet tissue laminate being flushed into a toilet or otherwise contacted by tap water. "Stable" as used herein means continuing to hold the fibers of the wet tissue laminate together as intended for use of the wet tissue laminate.

The liquid wetting composition can be any liquid that can be absorbed into the wet tissue laminate and may include any suitable components that provide the desired wiping properties. For example, the solution may include water, emollients, surfactants, fragrances, preservatives, organic or inorganic acids, chelating agents, pH buffers, or combinations thereof, as are well known to those skilled in the art. Further, the wetting composition may also contain lotions, medicaments, and/or antimicrobials. The wetting composition may contain additional agents that impart a beneficial effect on skin or hair and/or further act to improve the aesthetic feel of the compositions and wipes described herein. Examples of suitable skin benefit agents include emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

The wetting composition may be incorporated into the wet tissue laminate in an add-on amount of from about 10 to about 600 percent, more desirably from about 100 to about 500 percent, and even more desirably from about 200 to about 300 percent of the dry weight of the substrate. In one example, the wetting composition contains water. The wetting composition can in particular embodiments contain water in an amount of from about 40 to about 99 percent of the total weight of the solution.

Figure 2:
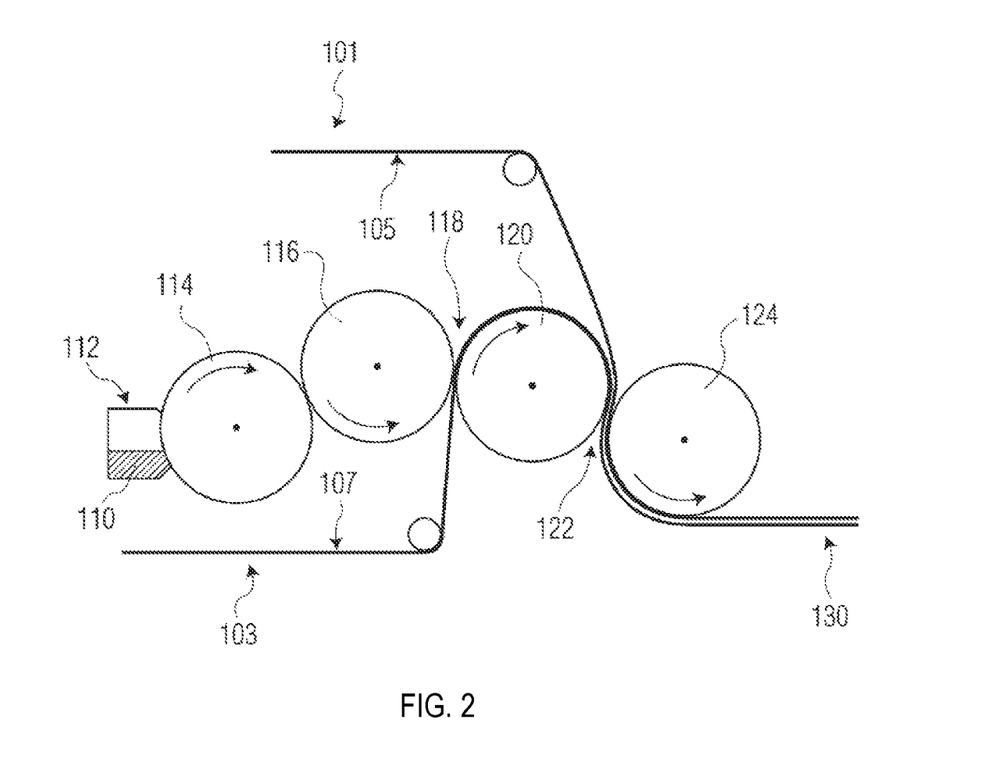
FIG. 2 is a schematic view of a process for manufacturing a dispersible wet wipe according to one embodiment of the present invention.

Turning now to FIG. 2, one method of manufacturing a tissue laminate according to the present invention is illustrated. The method includes providing first and second tissue plies 101, 103. Each ply having an outer surface 105, 107. At least one of the plies, preferably the bottommost ply, is supported by a belt, particularly a topographical belt, such as those described below, that supports and conveys the ply through the adhesive application process and through a nip.

An adhesive solution 110 is pumped into a reservoir or doctor chamber 112 and then applied onto antilox roll 114 by doctor chamber 112 using two doctor blades that keep the doctor chamber 112 sealed. The adhesive 110 is mechanically transferred from the anlilox roll 114 onto flexographic printing roll 116, which may be a rubber flexographic printing roll. A specific metered amount of the adhesive 110 is then transferred, due to capillary forces, out of the gravure cells on antilox roll 114 and onto flexographic printing roll 116. This flexographic printing roll 116, which may have an engraved pattern on its surface, contacts the outer surface 107 of the second ply 103 as the ply 103 passes through a nip 118 created by the flexographic printing roll 116 and a backing roll 120. As the ply 103 passes through the nip 118 the adhesive 110 is applied to its outer surface 107.

This second ply 103, now containing the adhesive 110 on its outer surface 107 is met by untreated first tissue ply 101, and the two plies 101, 103 are adhesively joined in a facing arrangement by passing through a second nip 122 formed between the backing roll 120 and a marrying roll 124. The two-ply, adhesively bonded, product 130 may be further converted in additional processes.

For ease of application, the adhesive may be dissolved in water, or in a non-aqueous solvent, such as methanol, ethanol, acetone, or the like, with water being the preferred solvent. The amount of binder dissolved in the solvent may vary depending on the polymer used and the application method. Desirably, the adhesive solution contains less than about 18 percent by weight of adhesive composition solids. More desirably, the adhesive solution contains less than 16 percent by weight of adhesive composition solids.

Figure 3:
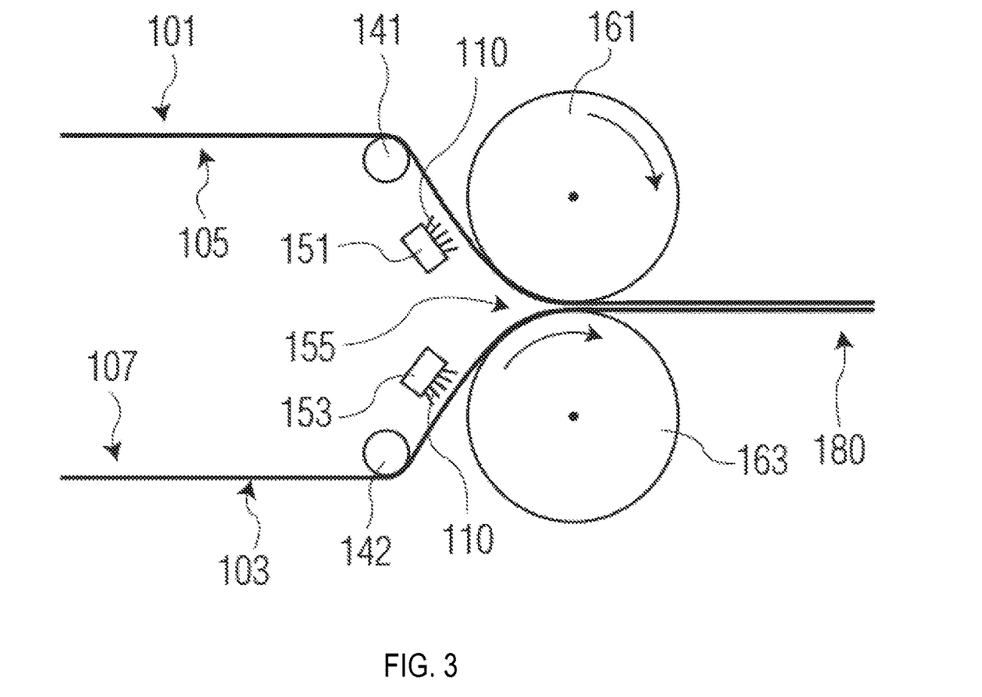
FIG. 3 is a schematic view of a process for manufacturing a dispersible wet wipe according to another embodiment of the present invention.

In alternative embodiments of the present invention, such as that illustrated in FIG. 3, the adhesive may be applied to the outer surfaces of one or more of the tissue plies by spraying. For example, individual tissue plies 101 and 103 are unwound from the reel stands and threaded over carrier rolls 141, 142. Preferably at least one of the plies, preferably the bottommost ply, is supported by a belt, particularly a topographical belt, such as those described below, that supports and conveys the ply through the adhesive application process and through a nip.

First and second spray assemblies 151, 153 are positioned between carrier rolls 141, 142 and a nip 155 created by opposed first and second rolls 161, 163. The spray assemblies 151, 153 are further positioned beneath, and across the width of (i.e. transverse to the movement of) each of the individual tissue plies 101 and 103 to spray an adhesive 110 to an outer surface 105, 107 of each ply 101, 103.

The spray assemblies may include a row of nozzles positioned in a housing which extends across the width of the web. Nozzles may be spaced apart from one another to provide the desired degree of coverage and in certain instances may be positioned such that any given point on the web generally receives output from two nozzles. Each nozzle is generally connected to an adhesive supply and atomizing air supply and a control air supply. The housing may include an axle that extends across the width of the housing and controls the rotation of a baffle plate. The housing may also include a trailing lip extending from the rear (trailing) edge.

The adhesive 110 applied by the first and second spray assemblies 151, 153 may have the same chemical composition, and perhaps even the same level of concentration prior to application. In other embodiments the chemical composition of the adhesives is different, and they are applied at different add-on levels. In still other embodiments, adhesive 110 applied by the first and second spray assemblies 151, 153 may be applied in the same pattern or may be applied in different patterns to the outer surface 105, 107 of each ply 101, 103.

Figure 4:
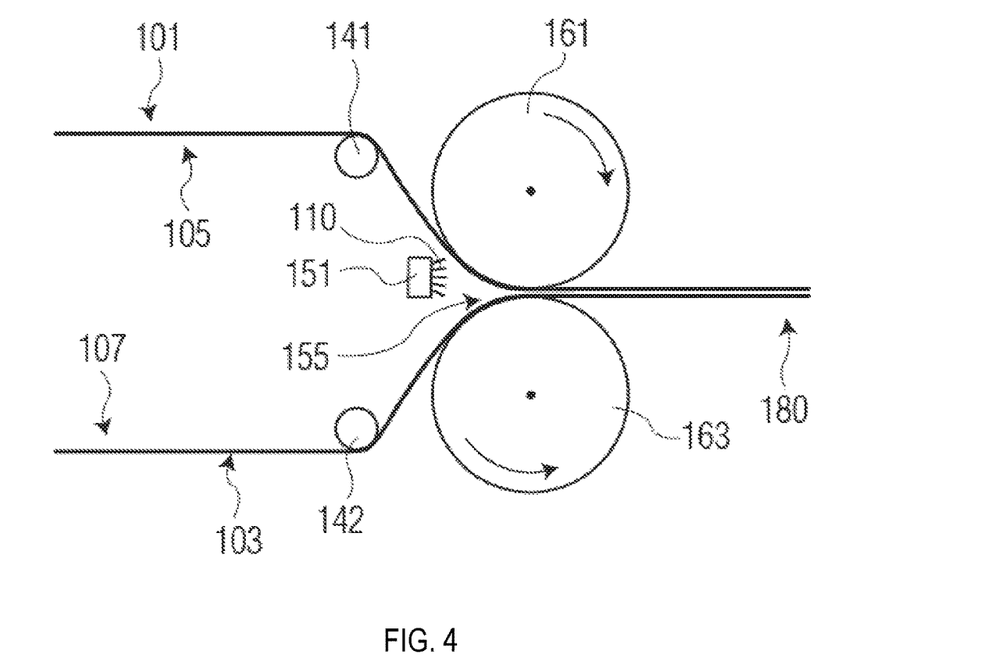
FIG. 4 is a schematic view of a process for manufacturing a dispersible wet wipe according to yet another embodiment of the present invention.

In other embodiments, such as that illustrated in FIG. 4, the laminate 180 is produced using a single spray assembly 151 that is positioned to apply adhesive 110 to the outer surfaces 105, 107 of each web 101, 103 immediately prior to a nip 155. Individual tissue webs 101 and 103 are unwound from the reel stands and threaded over carrier rolls 141, 142. At least one of the plies, preferably the bottommost ply, is supported by a belt, particularly a topographical belt, such as those described below, that supports and conveys the ply through process. The single spray assembly 151 is positioned between the carrier rolls 141, 142 and the nip 155 to spray adhesive 110 onto the outer surfaces 105, 107. After adhesive 110 is sprayed onto the outer surface 105, 107 of each ply 101, 103 they are combined in facing arrangement as they pass through a nip 155.

The nip 155 may be formed by a pair of opposed rolls 161, 163, which in certain instances may be urged against one another to apply a pressure to the nip. Formation of nips in this manner is common in the converting of tissue products and generally, it is desirable to load these rolls to one another at a set force. One of skill in the art will recognize this to be known generally as the nip force and is generally provided (or referenced) in terms of force per unit length. By convention herein, the units are known as pounds per linear inch (PLI or pli). In certain embodiments the force observed between the pair of opposed rolls 161, 163 is at least about 100 pli, such as at least about 150 pli, such as at least about 200 pli, such as at least about 300 pli. In certain instances the nip force may range from about 100 to about 500 pli, such as from about 200 to about 400 pli, such as from about 300 to about 400 pli.

In certain embodiments the nip may be in the form of a conventional embossing nip comprising a pair of opposed rolls where one of the rolls comprising an embossing pattern and the other is substantially smooth. For example, the first roll may have a substantially smooth surface comprising a deformable material, such as rubber, and more particularly EPDM or NBR (acrylonitrile-butadiene rubber) and having a hardness between 20 and 85 Shore A, preferably between 35 and 60 Shore A. The second roll may be a steel roll having a topographical pattern disposed thereon. The second roll may be made by any suitable process known in the art. Non-limiting examples of suitable processes include laser engraving hard plastic (ebonite) or ceramic or other material suitable for laser ablation to remove material and create embossing elements, chemical engraving of steel or other materials to remove material and create embossing elements, machining aluminum or steel or other metals to remove material and create embossing elements, metallizing processes to build up embossing elements, sintering processes to build up embossing elements and/or other means known in the art to remove material or build up material and achieve a surface topography with the desired pattern and clearances between mating embossing elements.

Embossing patterns useful in the present invention generally comprise a plurality of discrete dot embossing elements. Examples of suitable dot embossment shapes include circles, ovoid and squares having an aspect ratio of from 1 to about 1.25, such as from about 1 to about 1.1. These embossments may be homogeneous in size and shape or can vary within a given pattern. In certain instances the area of the roll surface covered by embossing elements may range from about 5 to about 50 percent. The density of the elements can be varied within the foregoing coverage ranges but are generally at least about 10 embossments/cm$^2$, such as from about 10 to about 100 embossments/cm$^2$, such as from about 20 to about 80 embossments/cm$^2$.

The protrusions forming the dot emboss elements may have a size from between about 0.5 to about 1.5 mm, such as from about 0.8 to about 1.2 mm. As used herein, "size" refers to the measurement of the shortest dimension of the emboss element. The angle of the sidewalls of the emboss elements may range from about 0 to about 25 degrees, such as from about 0 to about 15 degrees.

In certain embodiments the pattern of micro-embossments can be oriented so that the tops of the micro-embossments protrude from the tissue ply and form upper most surface plane of the ply or they can be oriented inward so that they face the interior of the product and may contact another ply and be bonded thereto with an adhesive.

Figure 5:
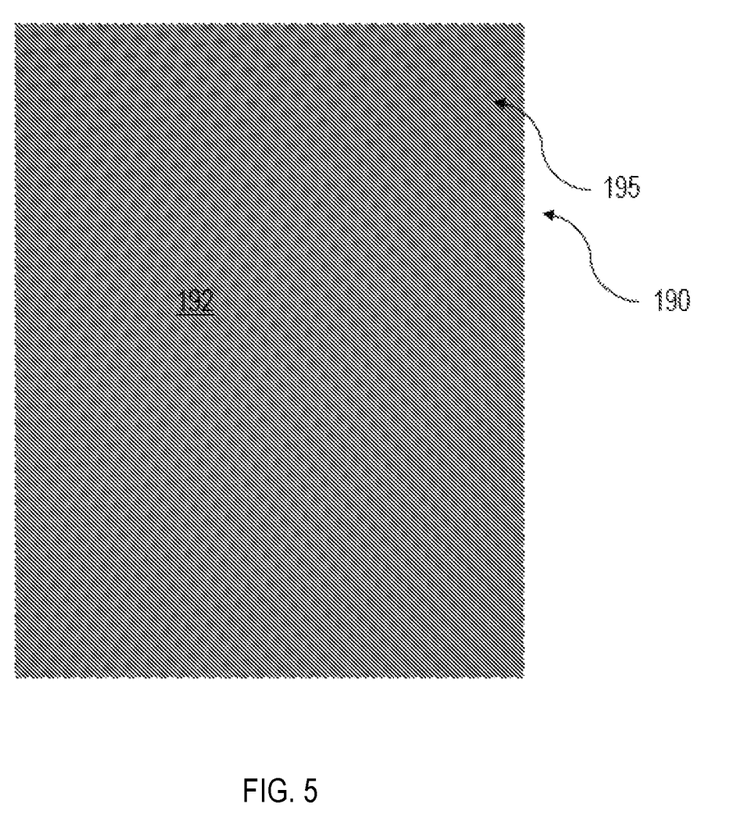
FIG. 5 is a top plan view of an embossing roll useful in the present invention.

FIG. 5 depicts one embossing pattern 190 for use in the products of the present disclosure, particularly an embossing pattern disposed on the bottommost ply of a product. Generally the pattern 190 will be disposed on the roll surface 192 in a uniform manner such that the pattern 190 contains a continuous and regular pattern of dot embossments 195. The pattern 190 as shown in FIG. 5, contains embossments 190 of a single size, however, the invention is not so limited, and the pattern may comprise dot embossments of different sizes.

In an alternate embodiment one of the plies may be supported by a topographical belt during the manufacturing process and particularly as the plies are joined together by passing through a nip. In particularly preferred embodiments the bottommost ply is in contact with, and supported, by a topographical belt, which in-turn is brought into contact with the bottom most roller as the plies are conveyed through the nip. The topographical belt may comprise a plurality of discrete protuberances extending from the web contacting surface of the belt and into the bottom most ply as it conveyed through the nip. Without being bound by any particular theory, it is believed that as the plies pass through the nip supported by the topographical fabric the protuberances cause elevated localized areas of pressure causing the plies to become bonded to one another at discrete locations corresponding to the protuberances. In this manner, the degree of bonding between the plies may be controlled to a certain extent by the shape, size and density of protuberances and the pressure of the nip.

The topographical belt, which may also be referred to herein as the carrier belt, will have protuberances covering only a portion of the belt surface area, such as less than about 50 percent, such as less than about 40 percent, such as less than about 30 percent, so that the area of the ply supported by the protuberance as it is conveyed through the nip experience a relatively high compression load. In particular, a lower protuberance surface contact area will allow for the forces applied along the length of the calendar rolls (measured in PLI), or transverse to the longitudinal direction of the carrier fabrics, to be more concentrated at discrete locations of the ply surface to achieve higher nip pressures with lower loading pressures.

Preferably the protuberances are discrete and the density of protuberances (the number of protuberances per square area unit of fabric surface area) ranges from about 10 to about 100 protuberances/cm$^2$, such as from about 20 to about 80 protuberances/cm$^2$, such as from about 30 to about 60 protuberances/cm$^2$. The height of the protuberances, which is the z-directional distance between the top plane of the protuberance and the lowest fabric surface contacted by the ply in-use, may range from about 0.5 to 2.5 mm, such as form about, 0.75 to about 2.25 mm, such as from about 1.00 to about 2.00 mm The topographical belt may be woven, non-woven or some combination of woven and non-woven. The belt may be air permeable or substantially impermeable. In certain preferred embodiments the topographical belt is an air permeable woven fabric. Woven fabrics may be produced using techniques well known in the art by interweaving warp and shute filaments to form protuberances, particularly discrete protuberances, having a protuberance height from about 0.5 to about 2.5 mm, such as form about 0.75 to about 2.25 mm, such as from about 1.00 to about 2.00 mm.

In a particularly preferred embodiment the belt is a multi-layered woven fabric having a load-bearing layer which integrates the fabric while providing sufficient strength to maintain the integrity of the fabric as it travels through the nip, and yet is sufficiently porous to enable air to flow through the fabric. The ply contacting surface of the fabric has a sculpture layer consisting predominantly of discrete which project substantially above the sub-level plane between the load-bearing layer and the sculpture layer. The protuberance comprise multiple warps (strands substantially oriented in the machine direction) which float above the sub-level plane and group together to form protuberances which are preferably wider and higher than the individual warps. The individual warp floats are interwoven with the load-bearing layer at their opposite ends. The protuberances may be discrete and spaced apart from one another forming land areas that surround the protuberances. The shape, size and spacing of the protuberances may be controlled to some extent by the weave pattern and the size of individual warp floats.

Figure 6:
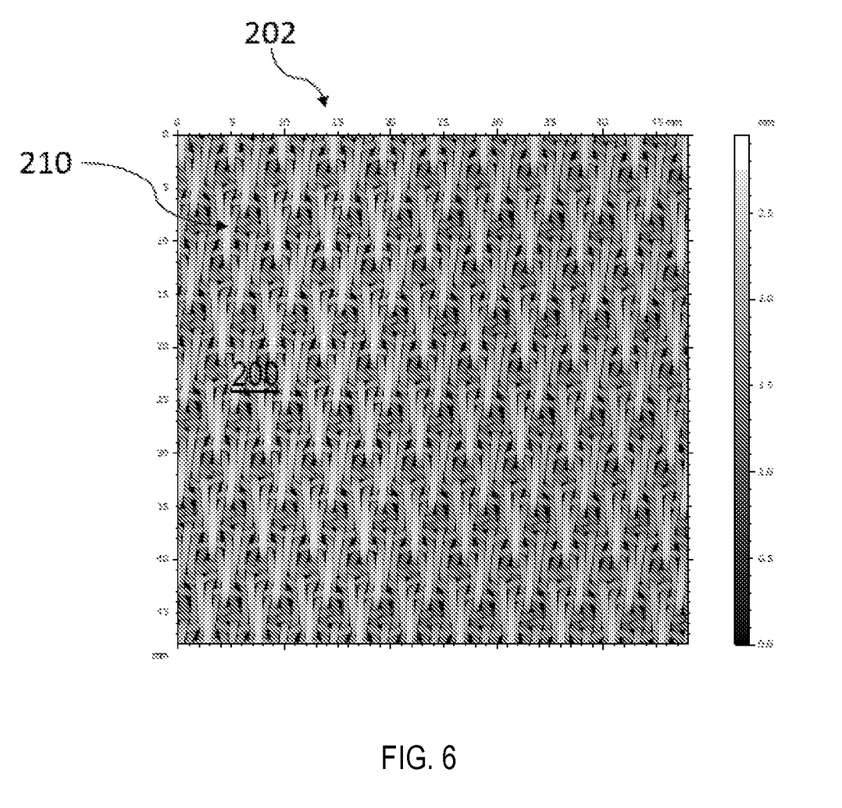
FIG. 6 is a is a profilometry scan (48 mm×48 mm) of a belt useful in the present invention taken using an FRT MicroSpy® Profile profilometer (FRT of America, LLC, San Jose, Calif.)

One particular topographical belt useful in the present invention is illustrated in FIGS. 5 and 6. the ply contacting surface 202 of the fabric 202 comprises a plurality of discrete protuberances 210 generally having a V-shape and orientated substantially in the machine direction. The protuberances 210 are generally disposed on the ply contacting surface 202 for cooperating with, and applying pressure to, the ply during manufacturing. In certain embodiments protuberances may be disposed on the web contacting surface in a pattern comprising a repeating motif protuberances having substantially similar shape, size and orientation.

In one particularly preferred embodiment, multi-ply adhesively bonded laminate is conveyed through a dryer to cure the adhesive. In certain instances, the multi-ply adhesively bonded laminate may be transferred to a through-air dryer fabric and conveyed over a through-air dryer to dry the laminate and/or cure the adhesive. In some embodiments, the through-drying fabric is a course, highly permeable, fabric. In alternative embodiments, other methods may be used as a substitute for, or in conjunction with, the through-air dryer to dry the laminate and/or cure the adhesive. For example, in some embodiments the through-air dryer may be used without a fabric. In other suitable embodiments of the disclosure, other drying systems known in the art (i.e., other than a through-air dryer system, e.g., drying cans, infra-red (IR), ovens) may be used so long as they do not deviate from the scope of this disclosure.

When using an ethylene vinyl acetate copolymer adhesive, the drying apparatus can be heated to a temperature of between about 120 to about 170° C.

The dried and/or cured laminate may be wound into a roll or reel. After winding, subsequent converting steps known to those of skill in the art can be used to transform the textured air laid substrate into a plurality of wet wipes. For example, the textured air laid substrate can be cut into individual wipes, the individual the wet tissue laminates folded into a stack, the stack of wet wipes moistened with a liquid wetting composition, and then the stack of wet wipes can be placed into a dispenser.

In certain embodiments the dispersible wet wipe of the present invention has a cross-machine direction wet tensile strength ("CDWT") of greater than 150 g/in, more particularly greater than 175 g/in, and more particularly great than 200 g/in, such as from about 150 to about 300 g/in, such as from about 175 to about 250 g/in. Having a CDWT strength in this range can help prevent the wet tissue laminate from tearing during dispensing or during personal hygiene use.

In yet other embodiments adhesively bonding the tissue plies together to form a dispersible laminate provides the laminate with improved tensile strength, particularly improved geometric mean wet tensile strength (GMWT). Desirably, the dispersible wet wipes have a GMWT strength of at least about 250 g/in, such as at least about 275 g/in, such as at least about 300 g/in, such as from about 250 to about 500 g/in, such as from about 275 to about 450 g/in.

In particular embodiments, the wet tissue laminate has a CDWT after soaking for 15 minutes in room temperature tap water of less than 100 g/in, such as from about 50 to about 100 g/in. In other embodiments, the wet tissue laminate preferably has a 60-min post-soak CDWT of less than 80 g/in, and more preferably less than 65 g/in. Having a post-soak CDWT in this range bears on the wet tissue laminate's ability to lose strength and break down in wastewater conveyance infrastructure after flushing, as the minimum time that a wipe would reside in a home drain line after being flushed is 15 minutes (although typically wipes reside in the home drain line longer than 15 minutes).

In still other embodiments, the present invention provides a dispersible wipe comprising two or more wet-laid tissue layers adhesively bonded to one another having a CDWT of greater than 200 g/in, more particularly greater than 225 g/in, and more particularly great than 250 g/in, and a Slosh-Box Break-Up Time of less than about 60 minutes, more particularly less than about 45 minutes, and more particularly less than about 30 minutes, in accordance with the test procedure set forth below.

In yet other embodiments the laminates of the present invention may have cup crush values that are comparable or lower than prior art wipes, particularly when comparing wipes having similar tensile strengths. Generally, lower cup crush values indicate an increased feeling of gentleness and softness of the wipe as it glides across the skin. Accordingly, laminates prepared according to the present invention may have cup crush values of about 75 gf or less, such as about 70 gf or less, such as about 65 gf or less, such as from about 50 to about 75 gf. Generally, the foregoing cup crush values may be achieved at a GMWT strength of at least about 250 g/in, such as at least about 275 g/in, such as at least about 300 g/in, such as from about 250 to about 500 g/in, such as from about 275 to about 450 g/in.

TEST METHODS

Dry Basis Weight

Prior to measuring the basis weight of dry tissue samples, such as basesheet used to manufacture the wet laminates of the present invention, dry samples are conditioned under TAPPI conditions (23±1° C. and 50±2 percent relative humidity) for a minimum of 4 hours. Basis weight of sample is measured by selecting twelve (12) products (also referred to as sheets) of the sample and making two (2) stacks of six (6) sheets. In the event the sample consists of perforated sheets of bath or towel tissue, the perforations must be aligned on the same side when stacking the usable units. A precision cutter is used to cut each stack into exactly 10.16×10.16 cm (4.0×4.0 inch) squares. The two stacks of cut squares are combined to make a basis weight pad of twelve (12) squares thick. The basis weight pad is then weighed on a top loading balance with a minimum resolution of 0.01 grams. The top loading balance must be protected from air drafts and other disturbances using a draft shield. Weights are recorded when the readings on the top loading balance become constant. The mass of the sample (grams) per unit area (square meters) is calculated and reported as the basis weight, having units of grams per square meter (gsm).

Wet Basis Weight

The basis weight of wet tissue products is measured by first recording the dimensions of the product in millimeters. Five (5) wipes are selected and hung to dry in an oven for 2 hours±5 minutes, at 105±2° C. (221±3.6° F.). After drying the samples are laid flat on a clean, dry work area and allowed to cool for 14±1 minute. Each wipe is then weighed to the nearest 0.01 gram and record the result. Basis weight is then calculated as follows:

$$\text{Basis Weight (gsm)} = \frac{(\text{Dry Weight (g)} - 0.135) \times 1{,}000{,}00}{\text{Length (mm)} \times \text{Width (mm)}}$$

The formula above attempts to correct for the amount of solids in a wetting solution hence 0.135 is deducted from the measured dry weight.

Dry Caliper

The caliper of dry tissue samples, such as basesheet used to manufacture the wet laminates of the present invention, is measured in accordance with TAPPI Test Method T 580 pm-12 "Thickness (caliper) of towel, tissue, napkin and facial products." The micrometer used for carrying out caliper measurements is an Emveco 200-A Tissue Caliper Tester (Emveco, Inc., Newberg, OR). The micrometer has a load of 2 kilo-Pascals, a pressure foot area of 2,500 square millimeters, a pressure foot diameter of 56.42 millimeters, a dwell time of 3 seconds and a lowering rate of 0.8 millimeters per second.

Wet Caliper

The caliper of wet tissue samples is measured using a micrometer having a platen with a 3 inch diameter (76.2 mm), a load of approximately 0.345 kilo-Pascals, and a dwell time of 3 seconds. Products are tested as-is. Five (5) representative samples were tested for each product or sheet and the arithmetic average of all individual samples tests was recorded as the appropriate Dry Tensile Dry tensile testing of dry tissue samples, such as basesheet used to manufacture the wet laminates of the present invention, is conducted on a tensile testing machine maintaining a constant rate of elongation and the width of each specimen tested is three (3) inches.

Dry tissue samples were prepared by first conditioning under TAPPI conditions for at least 4 hours and then cutting a 3±0.05 inch (76.2±1.3 mm) wide strip in either the machine direction (MD) or cross-machine direction (CD) orientation using a JDC Precision Sample Cutter (Thwing-Albert Instrument Company, Philadelphia, PA, Model No. JDC 3-10, Serial No. 37333) or equivalent.

The instrument used for measuring tensile strengths was an MTS Systems Sintech 11S, Serial No. 6233. The data acquisition software was MTS TestWorks® for Windows Ver. 3.10 (MTS Systems Corp., Research Triangle Park, NC). The load cell was selected from either a 50 Newton or 100 Newton maximum, depending on the strength of the sample being tested, such that the majority of peak load values fall between 10 to 90 percent of the load cell's full-scale value. The gauge length between jaws was 4 inches, the crosshead speed was 10±0.4 inches/min (254±1 mm/min), and the break sensitivity was set at 65 percent. The sample was placed in the jaws of the instrument, centered both vertically and horizontally. The test was then started and ended when the specimen broke. The peak load was recorded as either the "MD tensile strength" or the "CD tensile strength" of the specimen depending on direction of the sample being tested.

Ten representative specimens were tested, and the arithmetic average of all individual specimen tests was recorded as the appropriate MD or CD tensile strength having units of grams per three inches (g/3"). Tensile energy absorbed (TEA) and slope are also calculated by the tensile tester. TEA is reported in units of g·cm/cm$^2$ and slope is recorded in units of kilograms (kg). Both TEA and Slope are directionally dependent and thus MD and CD directions are measured independently.

Wet Tensile

Tensile testing of wet tissue samples, such as laminates of the present invention, is conducted on a tensile testing machine maintaining a constant rate of elongation and the width of each specimen tested is one (1) inch. Generally products are tested in their product forms without separating into individual plies. For example, a 2-ply product is tested as two plies and recorded as such. The tensile tester, which is the same as described above, parameters are as follows:

TABLE 1

| | |
|---|---|
| Crosshead Speed | 304.8 ± 10 mm/min (12 ± 0.4 inch/minute) |
| Gage Length | 76 ± 1 mm (3 ± 0.04 inch) |
| Load Units | Gram-force |
| Full-Scale Load | Use an appropriate load cell for the material being tested so the values fall between 5 and 95 percent of the full-scale load. |
| Break Sensitivity | 70% |
| Slope Preset Points | 70 and 157 grams |

In certain instances, prior to testing, samples may be soaked in a tap water at room temperature prior to testing. In such instances the samples are soaked in approximately 410 ml of room temperature tap water for each test specimen. The specimens and water are added to a container and are submerged for a specified period of time. At the end of the soak time, the samples are removed and tested immediately. The soak time in minutes, such as 10, 15, 30 or 60 minutes is noted along with the tensile reading.

Ten representative specimens are tested, and the arithmetic average of all individual specimen tests was recorded as the appropriate MD or CD tensile strength having units of grams per one inch (g/in).

Dispersibility

This test method evaluates the dispersibility of flushable consumer products, simulating travel through a wastewater conveyance system ("Slosh Box Test"). In this test method, a plastic tank is loaded with a product and 2 liters of tap water at room temperature. The container is then tipped back and forth at 26 oscillations per minute to simulate the movement of wastewater in the collection system. The time required for the wet tissue laminate specimen to break up entirely into pieces that measure at most approximately 1 sq. in. (6.5 sq. cm) is recorded. The amount of time to reach this point is measured ("Slosh-Box Break-Up Time"). The construction and motion of the apparatus is conducted as set forth in the "Guidelines for Assessing the Flushability of Disposable Nonwoven Products, Third Edition, FG502—Slosh Box Disintegration Test," available from the "Association of the Nonwovens Fabrics Industry," 1100 Crescent Green, Suite 115, Cary, NC, 27518, www.inda.org.

EXAMPLE

Samples were prepared to illustrate the benefits of forming a tissue laminate from plies having different properties. Each of the tissue laminates of the present example comprised two uncreped through-air dried ("UCTAD") tissue plies, which were manufactured substantially as described in U.S. Pat. No. 5,607,551, the contents of which are incorporated herein in a manner consistent with the present disclosure. The composition and physical properties of the dry tissue plies are set forth in Table 2, below.

TABLE 2

| | Ply Description | | | | |
|---|---|---|---|---|---|
| | Fiber Furnish (wt %) | Basis Weight (gsm) | GMT (g/3") | Caliper (mm) | Sheet Bulk (cc/g) |
| High BW NBSK | NBSK (100%) | 45.1 | 2423 | 0.84 | 18.5 |
| Low BW NBSK | NBSK (100%) | 35.2 | — | — | — |
| SSWK | SSWK (100%) | 30.1 | 870 | 0.72 | 24.0 |

Two-ply tissue laminates were made by spraying the plies with water and passing the plies through an embossing nip to join the plies together. Water was applied substantially as illustrated in FIG. 3. After being sprayed with water, the first and second tissue plies were brought into facing relation with one another and passed through a nip to form a bonded two-ply laminate. The nip was formed by a pair of opposed rolls, the upper roll comprising a rubber covered roll having a 40 P&J hardness and the lower roll comprised an engraved steel embossing roll. The bottom roll was heated to about 315° F. (157° C.). The pair of rolls were loaded against one another to provide a nip pressure of about 350 pli.

The embossing roll used to produce Codes 1-4 comprised a plurality of discrete dot-shaped elements substantially as illustrated in FIG. 5. The embossing roll used to produce Code 5 comprised a plurality of line-shaped emboss elements substantially as described in U.S. Pat. No. 10,422,083 and illustrated in FIG. 9 thereof. Further details regarding the various codes is provide in Table 3, below.

TABLE 3

| Code | Bottommost Ply | Uppermost Ply | Embossing Roll Design |
|---|---|---|---|
| 1 | High BW NBSK | SSWK | Discrete Dots |
| 2 | High BW NBSK | SSWK | Discrete Dots |
| 3 | High BW NBSK | SSWK | Discrete Dots |
| 4 | Low BW NBSK | Low BW NBSK | Discrete Dots |
| 5 | High BW NBSK | SSWK | Line Elements |

After exiting the nip, the laminate was passed through a series of dryers comprising a through-air dryer and an infra-red dryer operating from at about 220° C. at a speed of about 200 feet per minute (fpm) to dry the laminate.

A wetting composition comprising water and 2%, by weight of the composition, sodium chloride was added to the dried laminate at 215 percent of the weight of the dry laminate. The wetted web was converted into stacks of wipes and stored in moisture-impervious plastic bags until tested. The samples were subject to testing, as described herein, the results of which are summarized in Table 4, below.

TABLE 4

| | Code 1 | Code 2 | Code 3 | Code 4 | Code 5 |
|---|---|---|---|---|---|
| Dry Basis Weight (gsm) | 73.9 | 71.3 | 70.1 | 75.2 | 74.0 |
| Opacity | 48.09 | 49.44 | 51.09 | 53.67 | 49.36 |
| Dry Caliper (mm) | 0.55 | 0.57 | 0.69 | 0.54 | 0.63 |
| Wet Caliper (mm) | 0.50 | 0.52 | 0.6 | 0.48 | 0.53 |
| Wet Bulk (cc/g) | 6.8 | 7.2 | 8.4 | 7.1 | 6.4 |
| Cup Crush Peak Load (gf) | 73.32 | 65.21 | 58.42 | 83.65 | 75.75 |
| MD Tensile (30 min. soak) (g/in) | 154.9 | 152.7 | 157.7 | 119.4 | 99.1 |
| CD Tensile (4 min soak) (g/in) | 124.8 | 125.8 | 133.9 | 159.5 | 141.0 |
| MD Tensile (4 min soak) (g/in) | 287.7 | 368.6 | 403.8 | 368.4 | 276.7 |
| GMT (4 min soak) (g/in) | 189.4 | 215.3 | 232.5 | 242.4 | 197.5 |

EMBODIMENTS

First embodiment: A dispersible tissue laminate comprising a first wet-laid tissue ply and a second wet-laid tissue ply arranged in facing relation with one another, the first and second plies differing in respect to at least one of basis weight, sheet bulk, tensile strength or fiber composition; an adhesive; and a wetting agent.

Second embodiment: The laminate of the first embodiment wherein the tissue laminate has a geometric mean wet tensile strength (GMWT) greater than about 200 g/in and more preferably greater than about 250 g/in and a Slosh Time less than about 60 minutes.

Third embodiment: The laminate of the first or second embodiment wherein the first tissue ply and the second tissue ply are bonded together at a plurality of discrete bond points.

Fourth embodiment: The laminate of any one of the first through third embodiments wherein the first tissue ply comprises a wet-laid tissue ply having a geometric mean tensile (GMT) of about 900 g/3" or less and the second tissue ply comprises a wet-laid tissue ply having a GMT of about 1,200 g/3" or greater.

Fifth embodiment: The laminate of any one of the first through fourth embodiments wherein the first and second plies are through-air dried tissue plies and each ply has a dry basis weight from about 30 to about 50 gsm, wherein the basis weight of the first ply is less than the dry basis weight of the second ply.

Sixth embodiment: The laminate of any one of the first through fifth embodiments wherein the first and second tissue plies have different basis weights and the basis weight of the first ply is less than the basis weight of the second ply.

Seventh embodiment: The laminate of any one of the first through sixth embodiments wherein the first and second tissue plies differ in respect to fiber composition.

Eighth embodiment: The laminate of any one of the first through seventh embodiments wherein the tissue laminate has a cross-machine direction wet tensile strength (CDWT) greater than about 150 g/in.

Ninth embodiment: The laminate of any one of the first through eighth embodiments wherein the tissue laminate has a GMWT from about 175 to about 300 g/in, a CDWT from about 150 to about 250 g/in, and a Slosh Time less than about 20 minutes.

Tenth embodiment: The laminate of any one of the first through ninth embodiments wherein the adhesive add-on ranges from about 2.0 to about 10 gsm.

Eleventh embodiment: The laminate of any one of the first through tenth embodiments wherein the wetting composition add-on amount ranges from about 10 to about 600 percent by weight of the dry tissue laminate and the wetting composition comprises water and from about 0.4 and about 3.5 percent, by weight of the wetting composition, of an insolubilizing agent. In certain embodiments the insolubilizing agent comprises an inorganic salt or an organic salt.

Twelfth embodiment: The laminate of any one of the first through eleventh embodiments wherein the adhesive is a triggerable binder composition and is added at an add-on rate of between about 1 and about 4 percent based on the total weight of the dry laminate.

Thirteenth embodiment: The laminate of any one of the first through twelfth embodiments wherein the laminate has a cup crush value of about 75 gf or less and a GMWT of about 250 g/in or greater.

Fourteenth embodiment: The laminate of any one of the first through thirteenth embodiments wherein the laminate has a dry basis weight from about 70 to 80 gsm.

Fifteenth embodiment: The laminate of any one of the first through fourteenth embodiments wherein the laminate does not comprise thermoplastic fibers.

Sixteenth embodiment: The laminate of any one of the first through fifteenth embodiments wherein the laminate has a wet bulk of at least about 7.0 cc/g, such as from about 7.0 ta about 10.0 cc/g.

What is claimed is:

1. A dispersible tissue laminate comprising a first wet-laid tissue ply and a second wet-laid tissue ply arranged in facing relation with one another, the first and second plies having a dry basis weight from about 15 gsm to about 60 gsm and wherein the dry basis weight of the first and second plies differs by at least about 25%; an adhesive disposed as a plurality of discrete deposits between the first and second tissue plies; and a wetting composition at an add-on ranging from about 10 to about 600 percent, based upon the weight of the dry tissue laminate.

2. The laminate of claim 1 wherein the first tissue ply and the second tissue ply are bonded together at a plurality of discrete bond points by an adhesive at each of the plurality of discrete bond points.

3. The laminate of claim 1 wherein the first tissue ply has a dry basis weight ranging from about 25 gsm to about 30 gsm and the second tissue ply has a basis weight ranging from about 45 to about 50 gsm.

4. The laminate of claim 1 wherein the first and second plies are through-air dried tissue.

5. The tissue laminate of claim 1 wherein the fiber composition of the first and second tissue plies is different and the first ply comprises at least about 80%, by dry weight of the ply, Southern softwood kraft pulp and the second ply comprises at least about 80%, by dry weight of the ply, Northern softwood kraft pulp.

6. The laminate of claim 1 having a geometric mean wet tensile strength (GMWT) greater than about 250 g/in and a Slosh Time less than about 60 minutes.

7. The laminate of claim 1 having a GMWT from about 175 to about 300 g/in, a CDWT from about 150 to about 250 g/in and a Slosh Time less than about 20 minutes.

8. The laminate of claim 1 wherein the adhesive add-on ranges from about 2.0 to about 10 grams per square meter (gsm) of laminate.

9. The laminate of claim 1 wherein the wetting composition comprises water and from about 0.4 and about 3.5 percent, by weight of the wetting composition, of an insolubilizing agent.

10. The laminate of claim 1 further comprising a co-binder selected from the group consisting of poly(ethylene-vinyl acetate), poly(styrene-butadiene), poly(styrene-acrylic), a vinyl acrylic terpolymer, a polyester latex, an acrylic emulsion latex, polyvinyl chloride), ethylene-vinyl chloride copolymer, and a carboxylated vinyl acetate latex.

11. The laminate of claim 1 wherein the first ply has a first dry geometric mean tensile (GMT) and the second ply has a second GMT and wherein the second GMT is from about 30% to about 150% greater than the first GMT.

12. The laminate of claim 1 wherein the first ply has a GMT from about 600 g/3" to about 900 g/3" and the second ply has a GMT from about 1,200 g/3" to about 2,000 g/3".

13. A dispersible tissue laminate comprising:
   a. a first wet-laid tissue ply comprising at least about 80%, by weight dry weight of the tissue ply, Southern softwood kraft pulp and having a first geometric mean tensile strength ("GMT");
   b. a second wet-laid tissue ply comprising at least about 80%, by weight dry weight of the tissue ply, Northern softwood kraft pulp and having a second GMT, wherein the first and the second GMT differ by at least about 30%;
   c. an adhesive; and
   d. a wetting composition at an add-on ranging from about 10 to about 600 percent, based upon the weight of the dry tissue laminate,
   wherein the first and second tissue plies are bonded together at discrete bond points.

14. The laminate of claim 13 having a geometric mean wet tensile strength (GMWT) greater than about 250 g/in and a Slosh Time less than about 60 minutes.

15. The laminate of claim 13 having a GMWT from about 175 to about 300 g/in, a CDWT from about 150 to about 250 g/in and a Slosh Time less than about 20 minutes.

16. The laminate of claim 13 wherein the adhesive add-on ranges from about 2.0 to about 10 grams per square meter (gsm) of laminate.

17. The laminate of claim 13 wherein the wetting composition comprises water and from about 0.4 and about 3.5 percent, by weight of the wetting composition, of an insolubilizing agent and the add-on of wetting composition ranges from about 10 to about 600 percent by weight of the dry tissue laminate.

18. A method of making a dispersible adhesively bonded wet tissue laminate:
   a. providing a first wet-laid tissue ply having a first and a second surface and a GMT of about 900 g/3" or less;
   b. providing a second wet-laid tissue ply having a first and a second surface and a GMT of about 1,200 g/3" or greater;
   c. applying an adhesive to the first surface of the first wet-laid tissue ply;
   d. bringing the first surface of the first wet-laid tissue ply into facing relation with the first surface of the second wet-laid tissue ply;
   e. passing the first and second wet-laid tissue plies through a nip to form an adhesively bonded tissue laminate; and
   f. applying a wetting composition wetting composition to the adhesively bonded tissue laminate, wherein the add-on of the wetting composition ranges from about 10 to about 600 percent, based upon the weight of the dry tissue laminate.

19. The method of claim 18 further comprising the step of applying a second binder to the first surface of the second wet-laid tissue ply.

20. The method of claim 18 wherein the nip comprises a first roll having a substantially smooth surface and a second roll having an embossing pattern disposed thereon.

21. The method of claim 20 wherein the embossing pattern comprises a plurality of discrete dot embossments having an emboss element density from about 10 to about 60 embossments per square centimeter of roll surface area.

22. The method of claim 18 wherein the nip comprises first and second rolls loaded in opposition to one another at a load of at least about 100 pli and wherein at least the first or second roll is heated.

23. The method of claim 18 further comprising heat curing the laminate.

24. The method of claim 18 wherein the first and second tissue plies are through-air dried tissue plies having a basis weight from about 30 to about 60 gsm, wherein the basis weight of the first ply is less than the basis weight of the second ply.

25. The method of claim 18 further comprising the step of conveying the second wet-laid tissue ply through the nip on a continuous topographical belt having a plurality of protuberances disposed on its ply contacting surface.

26. The method of claim 25 wherein the continuous topographical belt comprises a woven fabric comprising at least about 50 protuberances per square centimeter of fabric surface area.

27. The method of claim 25 wherein the protuberances are discrete and have a protuberance height of at least about 1.00 mm.

* * * * *